(12) United States Patent
Ku et al.

(10) Patent No.: US 8,846,758 B2
(45) Date of Patent: *Sep. 30, 2014

(54) METHODS OF DECREASING GLYCOSYLATED HEMOGLOBIN IN PATIENTS WITH DYSLIPIDEMIA

(75) Inventors: Mannching Sherry Ku, Thiells, NY (US); Chih-Kuang Chen, Taipei (TW); Wei-Shu Lu, New Taipei (TW); Chih-Ming Chen, Taipei (TW); I-Yin Lin, Taipei (TW)

(73) Assignee: TWi Biotechnology, Inc., Taipei (TW)

( * ) Notice: Subject to any disclaimer, the term of this patent is extended or adjusted under 35 U.S.C. 154(b) by 59 days.

This patent is subject to a terminal disclaimer.

(21) Appl. No.: 13/553,271

(22) Filed: Jul. 19, 2012

(65) Prior Publication Data

US 2013/0022610 A1 Jan. 24, 2013

Related U.S. Application Data

(60) Provisional application No. 61/509,591, filed on Jul. 20, 2011.

(51) Int. Cl.
| | | |
|---|---|---|
| *A01N 37/02* | (2006.01) | |
| *A01N 37/10* | (2006.01) | |
| *A61K 31/225* | (2006.01) | |
| *C07C 50/18* | (2006.01) | |
| *A61K 45/06* | (2006.01) | |
| *A61K 38/17* | (2006.01) | |
| *A61K 31/235* | (2006.01) | |

(52) U.S. Cl.
CPC .............. *A61K 31/235* (2013.01); *A61K 45/06* (2013.01); *A61K 38/1793* (2013.01); *Y10S 514/866* (2013.01)
USPC ............ 514/548; 514/569; 514/866; 552/208

(58) Field of Classification Search
None
See application file for complete search history.

(56) References Cited

U.S. PATENT DOCUMENTS

| 6,610,750 B1 | 8/2003 | Charbit et al. |
| 7,943,121 B2 | 5/2011 | Masat et al. |
| 2008/0292640 A1* | 11/2008 | Solinger et al. ............ 424/158.1 |
| 2010/0158905 A1 | 6/2010 | Pearlman et al. |

OTHER PUBLICATIONS

Ramos-Zavala, M.G. et al. Effect of diacerein on insulin secretion and metabolic control in drug-naïve patients with type 2 diabetes. Diabetes Care, 2011, vol. 34, p. 1591-1594.*

Malaguti, C. et al. Diacerhein downregulate proinflammatory cytokines expression and decrease the autoimmune diabetes frequence in nonobese diabetic (NOD) mice. International Immunopharmacology, 2008, vol. 8, p. 782-791.*

Mooradian, A.D. Dyslipidemia in type 2 diabetes mellitus. Nature Clinical Practice Endocrinology and Metabolism, 2009, vol. 5, No. 3, p. 150-159.*

Donath et al., "The use of interleukin-1-receptor antagonists in the treatment of diabetes mellitus", Nature Clin. Pract. Endocrinol Metab. 2008, vol. 4(5), pp. 1-6.

Ingle et al., "Effects of metformin in combination with glimepiride on $HbA_{1c}$ and body mass index in Indian patients with type 2 diabetes mellitus", Journal of Pharmacy Research 2010, 3(9), 99. 2177-2179.

Koliaki et al., "Ineretin-based therapy: a powerful and promising weapon in the treatment of type 2 diabetes mellitus", Diabetes Ther 2011, 2(2), pp. 101-121.

* cited by examiner

*Primary Examiner* — Robert Landsman
*Assistant Examiner* — Bruce D Hissong
(74) *Attorney, Agent, or Firm* — Wood, Phillips, Katz, Clark & Mortimer

(57) ABSTRACT

Methods for treating abnormal glycosylated hemoglobin (HbA1c) levels in a patient in need thereof, wherein the provided methods comprise administering to a patient in need a therapeutically effective amount of an Interleukin-1β modulator. Also, the invention provides compositions comprising at least one lipid modifying agent and an IL-1β modulator.

3 Claims, 1 Drawing Sheet

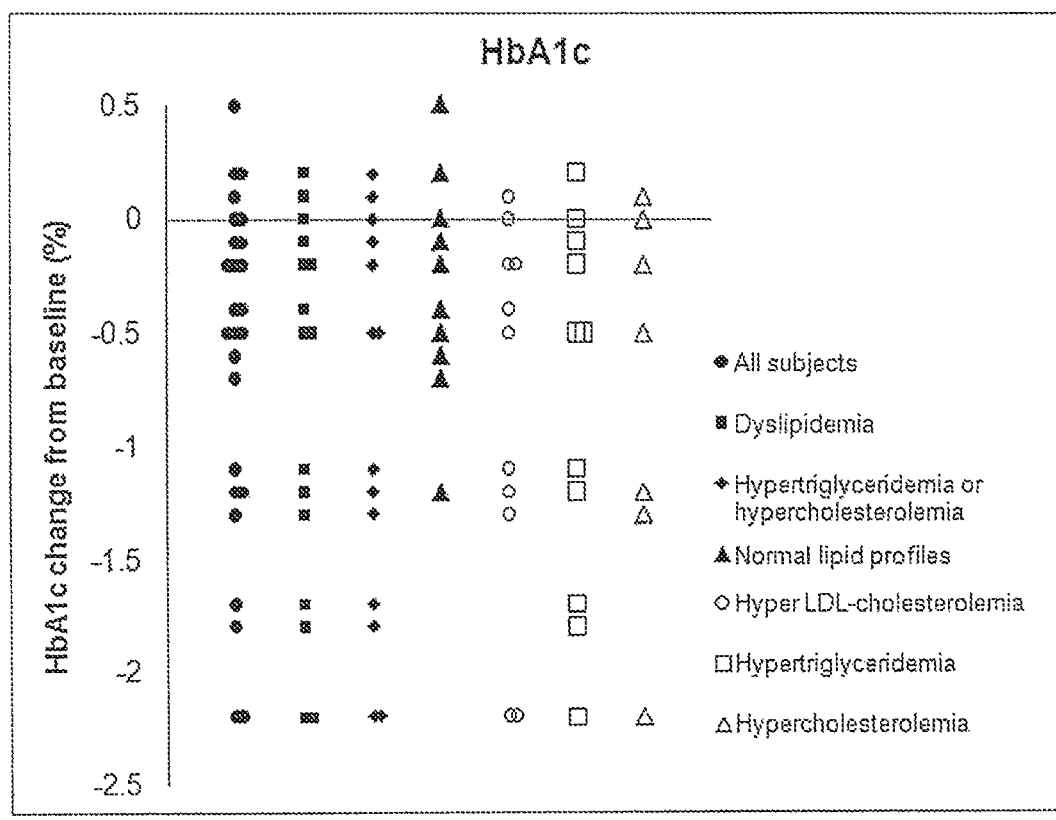

METHODS OF DECREASING GLYCOSYLATED HEMOGLOBIN IN PATIENTS WITH DYSLIPIDEMIA

BACKGROUND OF THE INVENTION

Dyslipidemia refers to a condition (or a group of conditions) wherein a patient has an abnormal amount of lipids in the blood. Most dyslipidemias are hyperlipidemias, including hypercholesterolemia, hyperglyceridemia, hyperlipoproteinemia and combined hyperlipidemia. Dyslipidemia may be manifested by an increase in the levels of total cholesterol, the low-density lipoprotein (LDL) cholesterol, the triglyceride concentrations, and a decrease in the high-density lipoprotein (HDL) cholesterol concentration in the blood.

Dyslipidemia is also one of the main risk factor for the development of diabetes. It has been shown to modulate β-cell function and survival. The influence of dyslipidemia on the β-cells of diabetic patients depends on a patient's specific lipid profile. Free fatty acids and lipoproteins have been shown to be pro-apoptotic for the β-cell. Lipoproteins may also similarly affect β-cell survival and function, whereby very-low-density lipoprotein (VLDL) and LDL are pro-apoptotic, while HDL is protective.

Dyslipidemia is also one of the major risk factors for cardiovascular disease in diabetes mellitus. In diabetic patients, 13% of men and 24% of women had increased total plasma cholesterol levels, 19% of men and 17% of women had increased plasma triglyceride levels, 9% of men and 15% of women had increased plasma LDL cholesterol levels, and 21% of men and 25% of women had decreased plasma HDL cholesterol levels. High levels of total cholesterol, LDL cholesterol and triglyceride were defined as values above the corresponding 90th percentile for the US population. The similar pattern of altered plasma lipid profiles is also observed in UK.

For adults with diabetes, it has been recommended that the levels of total cholesterol levels are less than 200 mg/dL (5.0 mmol/L), and that the levels of LDL, HDL, total cholesterol and triglyceride be measured every year. Optimal LDL cholesterol levels for adults with diabetes are less than 100 mg/dL (2.60 mmol/L), optimal HDL cholesterol levels are equal to or greater than 40 mg/dl (1.0 mmol/l) in men and 50 mg/dL (1.02 mmol/L) in women, and desirable triglyceride levels are less than 150 mg/dL (1.7 mmol/L).

For most patients, the dyslipidemia therapy commonly includes 1) lifestyle and nutrition intervention; 2) hydroxymethylglutaryl coenzyme A (HMG-CoA) reductase inhibitors, such as atorvastatin, cerivastatin, fuvastatin, lovastatin, mevastatin, pitavastatin, pravastatin, rosuvastatin and simvastatin; 3) niacin and derivatives, such as niceritrol, nicofuranose, aluminum nicotinate, nicotinyl alcohol and acipimox; 4) fibrates such as bezafibrate, aluminum clofibrate, gemfibrozil, fenofibrate, simfibrate, ronifibrate, ciprofibrate, etofibrate, clofibride and clinofibrate; 5) cholesterol absorption inhibitors, such as ezetimibe; 6) bile acid sequestrants, such as cholestyramine, colestipol, colestilan, colextran and colesevelam; 7) omega-3 fatty acid; and 8) cholesterylester transfer protein (CETP) inhibitors, such as anacetrapib, dalcetrapib and torcetrapib.

Interleukin-1β (IL-1β) is a pro-inflammatory cytokine associated with dyslipidemia and diabetes. Elevated levels of IL-1β in chronic dyslipidemia result in secretion of chemokines and other cytokines, increased expression of adhesion molecules, activation of endothelial and smooth muscle cell proliferation, macrophage activation, and increased vascular permeability.

IL-1β also inhibits β-cell function and promotes Fas-triggered apoptosis, in part by activating the transcription factor nuclear factor-κB (NF-κB). In vitro exposure of islets from nondiabetic organ donors to high glucose levels results in increased production and release of IL-1β, followed by NF-κB activation, Fas upregulation, DNA fragmentation, and impaired β-cell secretory function. The IL-1 receptor antagonist protects cultured human islets from these deleterious effects. β-Cells themselves were identified as the islet cellular source of glucose-induced IL-1β. In vivo, IL-1β-producing β-cells were observed in pancreatic sections of type 2 diabetic patients, but not in healthy subjects. These findings implicate an inflammatory process in the pathogenesis of glucotoxicity in type 2 diabetes and identify the IL-1β pathway as a target to preserve β-cell mass and function in this condition.

IL-1β modulators, such as IL-1 receptor antagonists, IL-1 Traps, human IL-1β monoclonal antibodys and IL-1β inhibitors, were previously shown to be useful for the treatment or prophylaxis of type 2 diabetes. However, no literature has reported that IL-1β modulators can improve the glycosylated hemoglobin (HbA1c) control in patients with dyslipidemia.

SUMMARY OF THE INVENTION

The present invention provides therapeutic methods to treat abnormal HbA1c levels in patients in need of such treatment, for example, patients with diabetes mellitus type 2 and dyslipidemia. The provided methods are especially suitable for diabetic patients who have inadequate medical control with current anti-diabetic therapies. Use of therapeutically effective amounts of IL-1β modulators, such as IL-1 receptor antagonists, IL-1 Traps, human IL-1β monoclonal antibodies, IL-1β inhibitors and pharmaceutically acceptable salts, analogs, prodrugs, or active metabolites thereof to treat abnormal HbA1c levels in patients with dyslipidemia offers unexpected advantages in decreasing abnormal blood HbA1c levels compared with diabetic patients with normal lipid profiles.

The provided therapeutic methods may optionally comprise administering an antidiabetic agent, such as sulfonylurea, biguanides, alpha-glucosidase inhibitors, thiazolidinediones (TZDs), peroxisome proliferator-activated receptor (PPAR) agonists, dipeptidyl peptidase-4 (DPP-4) inhibitors, nonsulfonylurea insulin secretagogues, glucagon-like peptide-1 (GLP-1) analogs, sodium-glucose transport proteins subtype 2 (SGLT2) inhibitors, and insulin.

The invention also provides a method of adjunctive treatment to treat abnormal HbA1c levels in a patient having diabetes mellitus type 2 and dyslipidemia, wherein said patient is undergoing treatment with at least one antidiabetic agent, said method comprising administering to said patient a therapeutically effective amount of an IL-1β modulator.

In one embodiment, the IL-1β modulator is selected from the group consisting of anakinra, rilonacept, canakinumab, gevokizumab, diacerin, and pharmaceutically acceptable salts, analogs, prodrugs, active metabolites and combinations thereof.

In a preferred embodiment, the IL-1β modulator is diacerin or a pharmaceutically acceptable salt, analog, prodrug or active metabolite thereof, and the therapeutically effective amount is equivalent to 25 to 200 mg of diacerin base per day.

In one embodiment, the active metabolite of diacerin is monoacetylrhein or rhein.

In one embodiment, the abnormal HbA1c levels are blood HbA1c levels above 7.0%.

The invention also provides a method for treating abnormal HbA1c levels in a patient in need thereof comprising administering to said patient at least one lipid modifying agent and a therapeutically effective amount of an IL-1β modulator.

In one embodiment, the lipid modifying agent is selected from the group consisting of HMG-CoA reductase inhibitors, niacin and niacin derivatives, fibrates, cholesterol absorption inhibitors, bile acid sequestrants, omega-3 fatty acids, cholesterylester transfer protein (CETP) inhibitors and combinations thereof.

The invention also provides a pharmaceutical composition for treating abnormal HbA1c levels comprising at least one lipid modifying agent and an IL-1β modulator.

BRIEF DESCRIPTION OF DRAWINGS

FIG. 1 is a graph showing that HbA1c levels in dyslipidemia patients decreased more than or equal to 0.5% compared to patients with normal lipid profiles.

DETAILED DESCRIPTION OF THE INVENTION

Use of therapeutically effective amounts of IL-1β modulators, such as IL-1 receptor antagonists, IL-1 Traps, such as rilonacept; human IL-1β monoclonal antibodies, such as canakinumab and gevokizumab; IL-1β inhibitors, such as diacerin and rhein and pharmaceutically acceptable salts, analogs, prodrugs, or active metabolites thereof to treat abnormal HbA1c levels in patients with dyslipidemia offers unexpected advantages in decreasing abnormal blood HbA1c levels compared with diabetic patients with normal lipid profiles.

IL-1β modulators, such as diacerin, can inhibit IL-1β synthesis, and down-modulate IL-1β induced activities. They have also been shown to possess disease modifying effect in experimental models of osteoarthritis and in human subjects with osteoarthritis of fingers, joints and knee. Thus, IL-1β plays a fundamental role in osteoarthritis pathophysiology and cartilage destruction. IL-1β also promotes expression of inducible nitric oxide synthase and increases release of prostaglandin E2, IL-6, IL-8 in human osteoarthritis chondrocytes. In diabetic patients with dyslipidemia, the levels of expression of pro-inflammatory factors such as IL-1β, IL-6 may be greater than those in diabetic patients with normal lipid profiles. Thus, diacerin (or other IL-1β modulators) may decrease the over-expression of pro-inflammatory factors in diabetic patients with dyslipidemia, and modulate β-cell function and survival. Therefore, the ability of IL-1β modulators, such as diacerin, to control levels of HbA1c is much better in diabetic patients with dyslipidemia than in diabetic patients with normal lipid profiles.

Further, IL-1β modulators, such as diacerin, may decrease the over-expression of pro-inflammatory factors in type 2 diabetic and dyslipidemic patients receiving at least one of anti-diabetic agents. This is especially so when the diabetes and/or dyslipidemia are inadequately controlled by anti-diabetic agents.

Thus, the invention also provides a method of adjunctive treatment to treat abnormal HbA1c levels in a patient having diabetes mellitus type 2 and dyslipidemia, wherein said patient is undergoing treatment with at least one antidiabetic agent, said method comprising administering to said patient a therapeutically effective amount of an IL-1β modulator.

As used herein, diacerin (4,5-bis(acetyloxy)-9,10-dioxo-2-anthracene carboxylic acid) refers to a compound having the following structural formula:

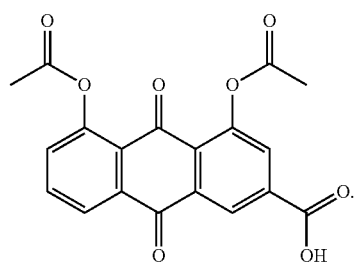 [SMILES: CC(=O)Oc1cccc2c1C(=O)c1c(OC(C)=O)cc(C(=O)O)cc1C2=O]

Pharmaceutically acceptable salts, prodrugs and active metabolites of diacerin are also contemplated for use in this invention. Pharmaceutically acceptable salts include salts of acidic or basic groups.

Rhein (9,10-dihydro-4,5-dihydroxy-9,10-dioxo-2-anthracenecarboxylic acid) and monoacetylrhein are known active metabolites of diacerin.

A prodrug is a pharmacologically inactive derivative of an active drug that is designed to convert into the active drug through in vivo physiological action, such as hydrolysis, metabolism and the like.

As used herein, the term "abnormal HbA1c levels" refers to human blood HbA1c levels above 7.0%.

The therapeutically effective amount of diacerin may vary with individual differences in age, weight, extent of diabetes, and the condition of the patient and can be determined by a skilled artisan. In a preferred embodiment of the invention, the therapeutically effective amount of diacerin is within the range of 25 to 200 mg per day. In a preferred embodiment, diacerin can be administered once or twice per day. The therapeutically effective amount of pharmaceutically acceptable salts, prodrugs, or active metabolites of the invention is preferably equivalent to 25 to 200 mg of diacerin base per day. The term "equivalent to 25 to 200 mg of diacerin base per day" refers to the amount of the pharmaceutically acceptable salts, prodrugs, or active metabolites which is necessary to achieve the same effect as provided by administering 25 to 200 mg of diacerin.

As used herein, the term "anti-diabetic agents" refers to drugs used to treat diabetes mellitus by lowering glucose levels in the blood. Examples of current available antidiabetic drugs include, but not limited to, sulfonylurea, biguanides, alpha-glucosidase inhibitors, thiazolidinediones (TZDs), dipeptidyl peptidase-4 inhibitors (DPP-4 inhibitors), nonsulfonylurea insulin secretagogues, glucagon-like peptide-1 analogs (GLP-1 analogs), sodium-glucose transport proteins subtype 2 inhibitors (SGLT2 inhibitors) and insulin. More specifically, the antidiabetic drugs include, but are not limited to metformin, glyburide, glimepiride, glipyride, glipizide, chlorpropamide, gliclazide, acarbose, miglitol, pioglitazone, troglitazone, rosiglitazone, isaglitazone, muraglitizar, peliglitazar, sitagliptin, saxagliptin, vildagliptin, alogliptin, linagliptin, dutogliptin, dutogliptin, repaglinide, nateglinide, mitiglindine, exenatide, liraglutide, albiglutide, canagliflozin, dapagliflozin, remogliflozin, sergliflozin and insulin. Those drugs can be given alone or in combination.

Combinational Therapies

In another embodiment, the invention also provides a method for treating abnormal HbA1c levels in a patient in need thereof comprising administering to said patient at least one lipid modifying agent and a therapeutically effective amount of an IL-1β modulator.

In one embodiment, the lipid modifying agent is selected from the group consisting of HMG-CoA reductase inhibitors, niacin and niacin derivatives, fibrates, cholesterol absorption inhibitors, bile acid sequestrants, omega-3 fatty acids, cholesterylester transfer protein (CETP) inhibitors and combinations thereof.

HMG-CoA reductase inhibitors include but are not limited to atorvastatin, cerivastatin, fluvastatin, lovastatin, mevastatin, pitavastatin, pravastatin, rosuvastatin, and simvastatin. Niacin and derivatives include but are not limited to niacin, niceritrol, nicofuranose, aluminum nicotinate, nicotinyl alcohol, and acipimox. Urate oxidase inhibitors include but are not limited to pegloticase, puricase, rasburicase and pegylated uricase. Fibrates include but are not limited to bezafibrate, aluminum clofibrate, gemfibrozil, fenofibrate, simfibrate, ronifibrate, ciprofibrate, etofibrate, clofibride and clinofibrate. Cholesterol absorption inhibitors include but are not limited to ezetimibe. Bile acid sequestrants include but are not limited to cholestyramine, colestipol, colestilan, colextran and colesevelam. CETP inhibitors include but are not limited to anacetrapib, dalcetrapib and torcetrapib.

Pharmaceutical Compositions

When administered to a subject in need thereof, diacerin, its pharmaceutically acceptable salts, prodrugs, or active metabolites can be prepared as pharmaceutical compositions. Pharmaceutical compositions contemplated for use in the invention can be in the form of a solid, solution, emulsion, dispersion, micelle, liposome and the like. The composition may be administered using any means known in the art, such as orally, nasally, parenterally, topically, transdermally, or rectally. Preferably, the composition is adapted for oral administration. For example, the drug can be mixed with suitable excipients for the preparation of tablets, capsules, pellets, troches, lozenges, solutions, powders or granules, suspensions, hard or soft capsules and any other forms suitable for use. The methods for preparing the pharmaceutical compositions and the selection of suitable excipients are readily understood by a skilled person in the art.

Combinational Formulations

The pharmaceutical compositions of diacerin, its pharmaceutically acceptable salts, prodrugs, or active metabolites can further comprise another active ingredient such as 1) an HMG-CoA reductase inhibitor; 2) niacin and derivatives; 3) a fibrate; 4) a cholesterol absorption inhibitor; 5) a bile acid sequestrant; 6) an omega-3 fatty acid; and 7) a CETP inhibitor.

Thus, in one embodiment, the invention provides a pharmaceutical composition for use in treating abnormal HbA1c levels, wherein the composition comprises diacerin and one or more of the following active ingredients: a HMG-CoA reductase inhibitor, niacin or its derivatives, a fibrate, a cholesterol absorption inhibitor, a bile acid sequestrant, an omega-3 fatty acid and a CETP inhibitor.

HMG-CoA reductase inhibitors include but are not limited to atorvastatin, cerivastatin, fluvastatin, lovastatin, mevastatin, pitavastatin, pravastatin, rosuvastatin, and simvastatin. Niacin and derivatives include but are not limited to niacin, niceritrol, nicofuranose, aluminum nicotinate, nicotinyl alcohol, and acipimox. Urate oxidase inhibitors include but are not limited to pegloticase, puricase, rasburicase and pegylated uricase. Fibrates include but are not limited to bezafibrate, aluminum clofibrate, gemfibrozil, fenofibrate, simfibrate, ronifibrate, ciprofibrate, etofibrate, clofibride and clinofibrate. Cholesterol absorption inhibitors include but are not limited to ezetimibe. Bile acid sequestrants include but are not limited to cholestyramine, colestipol, colestilan, colextran and colesevelam. CETP inhibitors include but are not limited to anacetrapib, dalcetrapib and torcetrapib.

The second active ingredient could be in a controlled-release dosage form or in an immediate release dosage form.

The following Example is provided solely to illustrate some embodiments of the invention. It is not meant to limit the invention in any way.

EXAMPLE 1

A Randomized, Double-Blind, Placebo-Controlled Study of Diacerin in Patients with Uncontrolled Type 2 Diabetes Mellitus Objectives:

To evaluate the efficacy and safety of diacerin for the treatment of type 2 diabetes mellitus (DM).

Primary Endpoints:

To compare the efficacy of add-on diacerin with no add-on treatment (placebo) on HbA1c after 24-week double-blind treatment in Type 2 DM patients inadequately controlled by previous antidiabetic therapy.

Subjects:

Male or female patients (BMI≤35 kg/m$^2$) with type 2 diabetes mellitus on a stable oral hypoglycemic monotherapy for at least 3 months prior to screening visit. The HbA1c measurements taken at screening visit must be between 7% and 12%. Patients enrolled in the study must be receiving one or more oral antihyperglycemic agents including sulfonylurea, biguanides, alpha-glucosidase inhibitors, thiazolidinediones, and nonsulfonylurea insulin secretagogues.

Procedure:

This was a prospective, randomized, double-blind, and parallel comparison study comparing diacerin 50 mg versus placebo in patients with type 2 diabetes mellitus inadequately controlled by previous antidiabetic therapy. The starting dose of diacerin was 50 mg once daily every morning for 4 weeks and could be adjusted up to 50 mg twice daily (morning and evening) if patients have become accustomed to the medication. Patients were screened for eligibility four weeks (week—4) prior to entry at baseline (week 0). During this 4-week screening period, the participants continued their previous antidiabetic therapy, dietary habits, and other lifestyle habits. In order to be eligible for randomization following the 4-week screening period, patients must not have experienced hypoglycemia and must have had two fasting plasma glucose (FPG) measurements of between 135 to 250 mg/dL. At the end of the screening period, patients who met eligibility requirements were randomly assigned to receive diacerin 50 mg or placebo twice a day for 24 weeks observation. During treatment/observation period, the previous antidiabetic therapy including the class and/or dosage was not changed. Patients were asked to attend the center on eight occasions (screening, baseline, week 4, 8, 12, 16, 20 and 24) during the trial. The total study duration including the screening period for each patient was 28 weeks. There was a two weeks long follow-up period after completion of the treatment/observation. During this follow-up period, patients were followed for adverse events.

Statistical Method(s) for Efficacy/Safety Evaluations:

The difference (diacerin vs. placebo) of HbA1c reduction between the two treatment groups was analyzed by analysis of covariance (ANCOVA) with baseline value as a covariate. The corresponding 95% confidence interval was calculated. Within-group changes were also analyzed, with paired t test used to evaluate differences from baseline in each treatment group.

levels greater than 150 mg/dl, or plasma LDL levels greater than 100 mg/dl at baseline respectively. Plasma cholesterol, triglyceride and LDL levels in the other 10 subjects were normal in the baseline. Thus, there were 16 subjects in the dyslipidemia subgroup.

After the 24-week treatment, diacerin was found to specifically decrease the HbA1c levels by about 0.63% compared with the placebo group (p<0.05). In the dyslipidemia subgroup, diacerin decreased the HbA1c levels by about 0.82% compared with the baseline. In contrast, in type 2 diabetic patients with normal lipid profile diacerin decreased the HbA1c levels by only about 0.30% compared with the baseline (Table 1).

TABLE 1

Diacerein Group
Laboratory parameter: HbA1c mean change from baseline (%)

| Subgroup | N | Mean LDL (mg/dl)[1] | Mean TG (mg/dl)[2] | Mean TC (mg/dl)[3] | HbA1c week 24 (%)[4] | P value[6] compared with the placebo group |
|---|---|---|---|---|---|---|
| All subjects | 26 | 96.61 | 174.54 | 173.04 | −0.63 | <0.05 |
| Dyslipidemia[5] | 16 | 114.64 | 214.88 | 196.69 | −0.82 | <0.05 |
| Hypertriglyceridemia or hypercholesterolemia | 14 | 115.26 | 233.36 | 199.57 | −0.89 | <0.05 |
| Hyper LDL-cholesterolemia | 11 | 126.02 | 213.09 | 212.27 | −0.84 | <0.05 |
| Hypertriglyceridemia | 11 | 110.45 | 268.91 | 194.45 | −0.83 | <0.05 |
| Hypercholesterolemia | 7 | 130.26 | 237.29 | 231.43 | −0.76 | <0.05 |
| Normal lipid profiles | 10 | 67.77 | 110.00 | 135.20 | −0.30 | >0.05 |

[1]Mean LDL level in baseline;
[2]Mean blood triglyceride level in baseline;
[3]Mean blood total cholesterol level in baseline;
[4]HbA1c mean change from baseline (%);
[5]Dyslipidemia: subjects with hypertriglyceridemia, hyper LDL-cholesterolemia or hypercholesterolemia;
[6]P value: t-test.

For the efficacy parameters, descriptive statistics were presented by visit. Statistical analysis was performed to assess the mean change from baseline. The area under the concentration-time curve (AUC) was used for evaluating the parameters measured by oral glucose tolerance test.

Adverse events were summarized according to the Medical Dictionary for Regulatory Activities (MedDRA) adverse event dictionary. The tabulations counted the number of patients reporting individual preferred term adverse events and the total number of patients reporting at least one adverse event per system organ class. If appropriate, the incidence of adverse events was compared for each of the two treatment groups using Fisher's Exact test.

Dyslipidemia Sub-Group Evaluations:

A dyslipidemia sub-group was assembled, wherein subjects had the following baseline levels: a) plasma cholesterol levels greater than 200 mg/dl, or b) plasma triglyceride levels greater than 150 mg/dl, or c) plasma LDL levels greater than 100 mg/dl. The effects of administering HbA1c to the patients in this dyslipidemia sub-group were analyzed by paired t-test compared with the placebo group.

Results are shown in Table 1. Subjects (n=76) were randomized in a 1:1 ratio to receive twice-daily diacerin 50 mg (n=38), or placebo (n=38) for 24 weeks. 26 subjects in the diacerin group finished the whole treatment period. Within these 26 subjects, there were 16 subjects with plasma cholesterol levels greater than 200 mg/dl, or plasma triglyceride After 24 weeks of treatment in the diacerin group, HbA1c levels in 13 of 26 patients (50%) decreased by more than or equal to 0.5%. In the dyslipidemia subgroup, HbA1c levels in 10 of 16 patients (62.5%) decreased by more than or equal to 0.5%. In the hypertriglyceridemia or hypercholesterolemia subgroup, HbA1c levels in 10 of 14 patients (71.4%) decreased by more than or equal to 0.5%. In the hypertriglyceridemia subgroup, HbA1c levels in 7 of 11 patients (63.6%) decreased by more than or equal to 0.5%. In the hypercholesterolemia subgroup, HbA1c levels in 4 of 7 patients (57.1%) decreased by more than or equal to 0.5%. In contrast, in only 4 of 10 patients (40%) with normal plasma lipid profiles, HbA1c levels decreased by more than or equal to 0.5%. (FIG. 1).

In this study, administration of diacerin resulted in no significant changes in body weight and lipid profiles compared with the placebo group.

This experiment demonstrates that diacerin can specifically reduce HbA1c levels in type 2 diabetic patients, especially in patients with dyslipidemia, but not influence the lipid profiles.

What is claimed is:

1. A method of adjunctive treatment of abnormal glycosylated hemoglobin (HbA1c) levels in a patient having diabetes mellitus type 2 and dyslipidemia, first comprising administering to said patient an antidiabetic agent and then administering to said patient a therapeutically effective amount of an interleukin-1b (IL-1b) modulator, wherein said IL-1b modulator is diacerin or a pharmaceutically acceptable salt, analog, prodrug or active metabolite thereof, and wherein said therapeutically effective amount is equivalent to 25 to 200 mg of diacerin base per day.

2. The method of claim 1, wherein said antidiabetic agent is one or more agents selected from the group consisting of sulfonylurea, biguanides, alpha-glucosidase inhibitors, thiazolidinediones (TZDs), peroxisome proliferator-activated receptor (PPAR) agonists, dipeptidyl peptidase-4 (DPP-4) inhibitors, nonsulfonylurea insulin secretagogues, glucagon-like peptide-1 (GLP-1) analogs, sodium-glucose transport proteins subtype 2 (SGLT2) inhibitors, and insulin.

3. The method of claim 1, wherein said active metabolite of diacerin is monoacetylrhein or rhein.

* * * * *

UNITED STATES PATENT AND TRADEMARK OFFICE
CERTIFICATE OF CORRECTION

Page 1 of 1

PATENT NO.         : 8,846,758 B2
APPLICATION NO.    : 13/553271
DATED              : September 30, 2014
INVENTOR(S)        : Ku et al.

It is certified that error appears in the above-identified patent and that said Letters Patent is hereby corrected as shown below:

In the Claims
In column 9, claim 3, line 15 please delete "diacerin" and replace it with --diacerein--.

Signed and Sealed this
First Day of March, 2016

Michelle K. Lee
*Director of the United States Patent and Trademark Office*